(12) United States Patent
Thibaut et al.

(10) Patent No.: US 9,986,947 B2
(45) Date of Patent: Jun. 5, 2018

(54) EVALUATION OF AN IMPLANTED PROSTHESIS

(71) Applicant: Cochlear Limited, Macquarie University, NSW (AU)

(72) Inventors: Kyun Thibaut, Brussels (BE); Jurgen Van Vlem, Borgerhout (BE); Christiane D'hondt, Kruibeke (BE); Florent Hubert-Brierre, Meise (BE); Kristof Buytaert, Wilrijk (BE); Hans Bernhard, Liebefeld (CH); Grégoire Meylan, Marly (CH); Martin Junghans, Suhr (CH); Susanne Gentner, Rheinfelden (CH)

(73) Assignee: Cochlear Limited, Macquarie University, NSW (AU)

( * ) Notice: Subject to any disclaimer, the term of this patent is extended or adjusted under 35 U.S.C. 154(b) by 239 days.

(21) Appl. No.: 13/650,716

(22) Filed: Oct. 12, 2012

(65) Prior Publication Data

US 2014/0107526 A1    Apr. 17, 2014

(51) Int. Cl.

| | |
|---|---|
| *H04R 29/00* | (2006.01) |
| *A61B 5/00* | (2006.01) |
| *A61F 11/08* | (2006.01) |
| *H04R 25/00* | (2006.01) |
| *A61B 7/00* | (2006.01) |
| *A61L 2/08* | (2006.01) |
| *A61L 2/07* | (2006.01) |
| *A61L 2/20* | (2006.01) |
| *A61B 5/12* | (2006.01) |

(52) U.S. Cl.
CPC .......... *A61B 5/4851* (2013.01); *A61B 5/6817* (2013.01); *A61B 7/005* (2013.01); *A61F 11/08* (2013.01); *A61L 2/07* (2013.01); *A61L 2/081* (2013.01); *A61L 2/206* (2013.01); *H04R 25/30* (2013.01); *H04R 25/606* (2013.01); *A61B 5/125* (2013.01); *A61B 5/4836* (2013.01); *A61B 5/7246* (2013.01); *A61F 2011/085* (2013.01); *H04R 25/604* (2013.01)

(58) Field of Classification Search
USPC .......................................................... 381/60
See application file for complete search history.

(56) References Cited

U.S. PATENT DOCUMENTS

| | | | | |
|---|---|---|---|---|
| 5,792,073 A * | 8/1998 | Keefe | ..................... | A61B 5/121 600/559 |
| 5,923,764 A * | 7/1999 | Shennib | ................. | A61B 5/121 381/23.1 |
| 6,342,035 B1 | 1/2002 | Kroll et al. | | |
| 6,366,863 B1 * | 4/2002 | Bye | ......................... | A61B 5/121 702/57 |
| 7,747,026 B2 | 6/2010 | Ball | | |
| 2003/0161482 A1 * | 8/2003 | Miller | ..................... | H04R 25/30 381/60 |
| 2004/0037428 A1 * | 2/2004 | Keller | ..................... | A61B 5/121 381/60 |
| 2008/0031465 A1 * | 2/2008 | Ball | ........................ | H04R 25/30 381/60 |

* cited by examiner

*Primary Examiner* — Amir Etesam
(74) *Attorney, Agent, or Firm* — Martin J. Cosenza; Pilloff & Passino LLP

(57) ABSTRACT

Evaluating an implanted hearing prosthesis, including operating the implanted hearing prosthesis, capturing sound generated by a transducer of the prosthesis during said operation, and comparing the captured sound to a sound model.

48 Claims, 17 Drawing Sheets

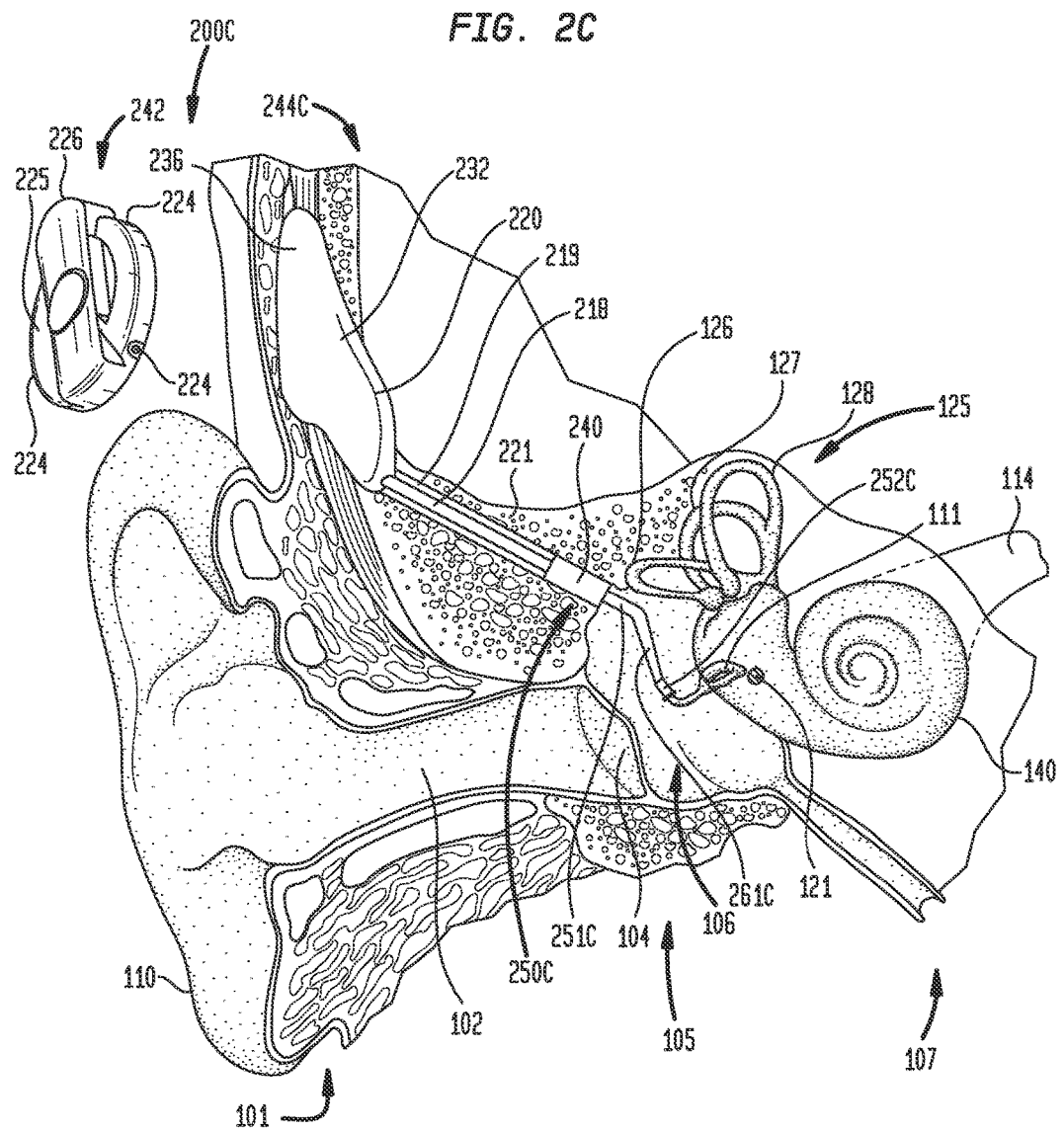

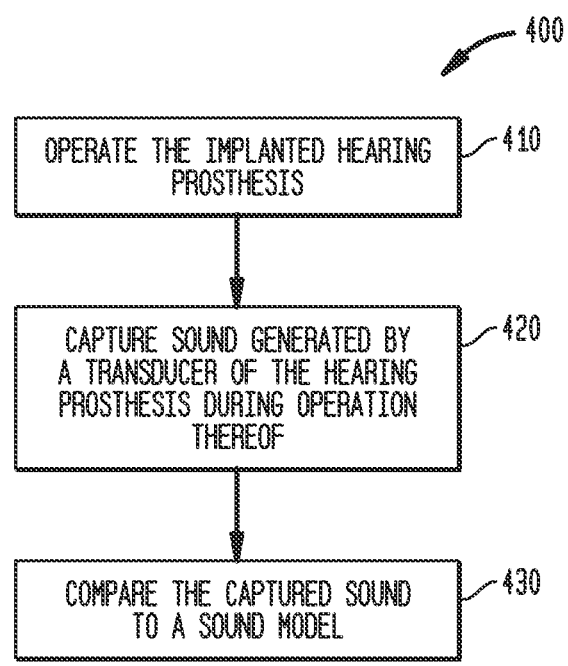

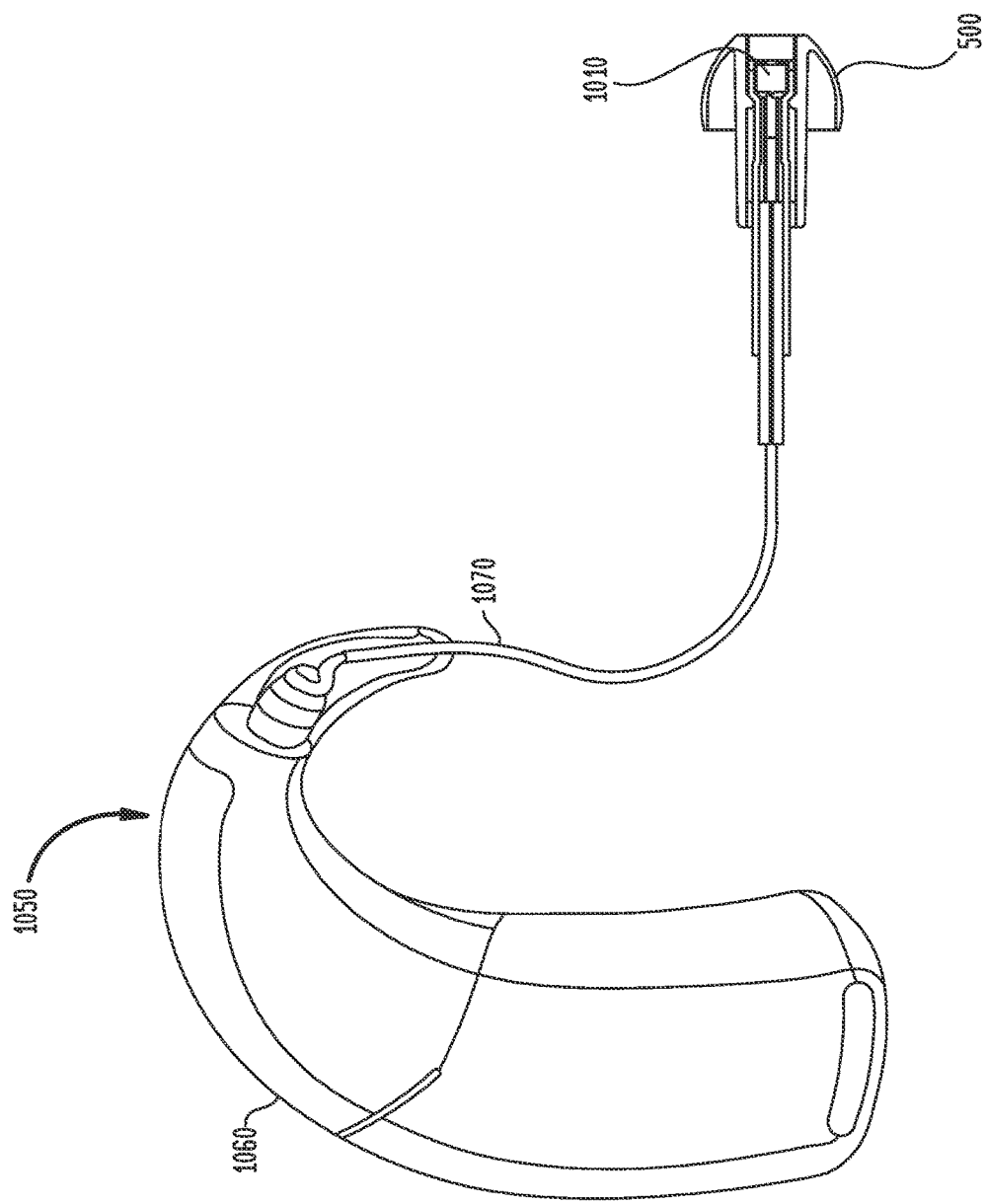

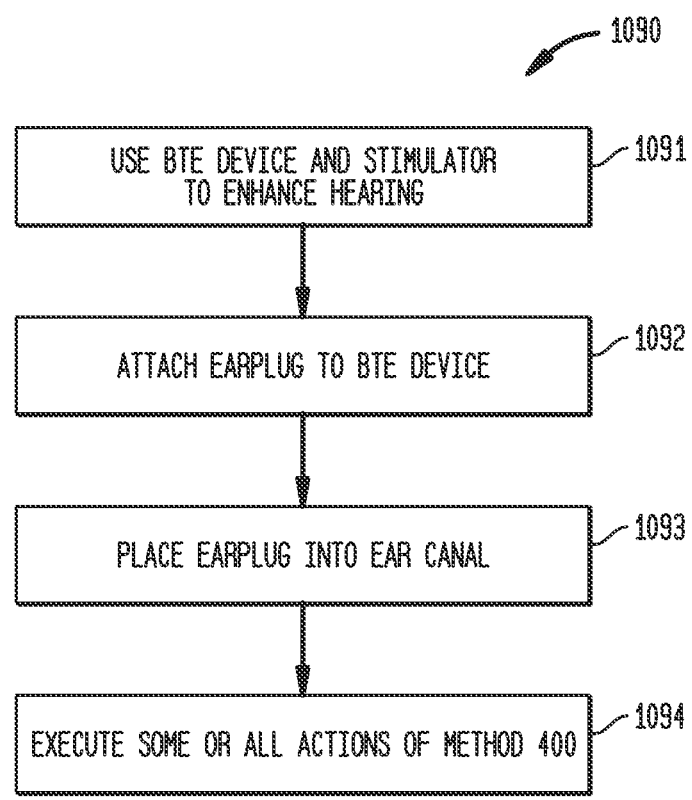

EVALUATION OF AN IMPLANTED PROSTHESIS

BACKGROUND

Field of the Invention

Embodiments of the present technology relate generally to prostheses such as active hearing prostheses, and more particularly, to the evaluation of an implanted prosthesis.

Related Art

Hearing loss is generally of two types, conductive and sensorineural. Sensorineural hearing loss is due to the absence or destruction of the cochlear hair cells which transduce sound into nerve impulses. Various hearing prostheses have been developed to provide individuals suffering from sensorineural hearing loss with the ability to perceive sound. For example, cochlear implants have an electrode assembly which is implanted in the cochlea. In operation, electrical stimuli are delivered to the auditory nerve via the electrode assembly, thereby bypassing the inoperative hair cells to cause a hearing percept.

Conductive hearing loss occurs when the natural mechanical pathways that provide sound in the form of mechanical energy to a cochlea are impeded, for example, by damage to the ossicular chain or ear canal. For a variety of reasons, such individuals are typically not candidates for a cochlear implant. Rather, individuals suffering from conductive hearing loss sometimes receive an acoustic hearing aid, and sometimes seek surgical options. Hearing aids rely on principles of air conduction to transmit acoustic signals to the cochlea. In particular, hearing aids amplify received sound and transmit the amplified sound into the ear canal. This amplified sound reaches the cochlea in the form of mechanical energy, causing motion of the perilymph and stimulation of the auditory nerve.

SUMMARY

Some aspects of the present technology are generally directed to an earplug, comprising an occluding apparatus configured to occlude an ear canal of a recipient, and a sound capture apparatus integrated with the occluding apparatus and having a sound receiver that faces the middle ear when the earplug is effectively positioned in the ear canal.

Some other aspects of the present technology are generally directed to a system for evaluating an implanted prosthesis having a vibrating diaphragm when in operation, comprising a sound capture apparatus configured to capture sound caused by the vibrating diaphragm traveling through a middle ear of a recipient, and to generate an audio signal representative of the captured sound, and a sound analyzer configured to compare the audio signal to a sound model.

Some other aspects of the present technology are generally directed to a method of evaluating an implanted prosthesis, comprising, operating the implanted prosthesis, capturing vibrations generated by a transducer of the prosthesis during said operation, and comparing the captured vibrations to a vibration model.

BRIEF DESCRIPTION OF THE DRAWINGS

Embodiments of the present technology are described below with reference to the attached drawings, in which:

FIG. 2C is a perspective view of an exemplary middle ear implant implanted in accordance with an embodiment;

FIG. 4 is a flowchart for an exemplary method in accordance with an embodiment;

FIG. 10B is an exemplary external component of a hearing prosthesis in accordance with an exemplary embodiment;

FIG. 10C is a flowchart for another exemplary method in accordance with an embodiment;

DETAILED DESCRIPTION

Figure 1:
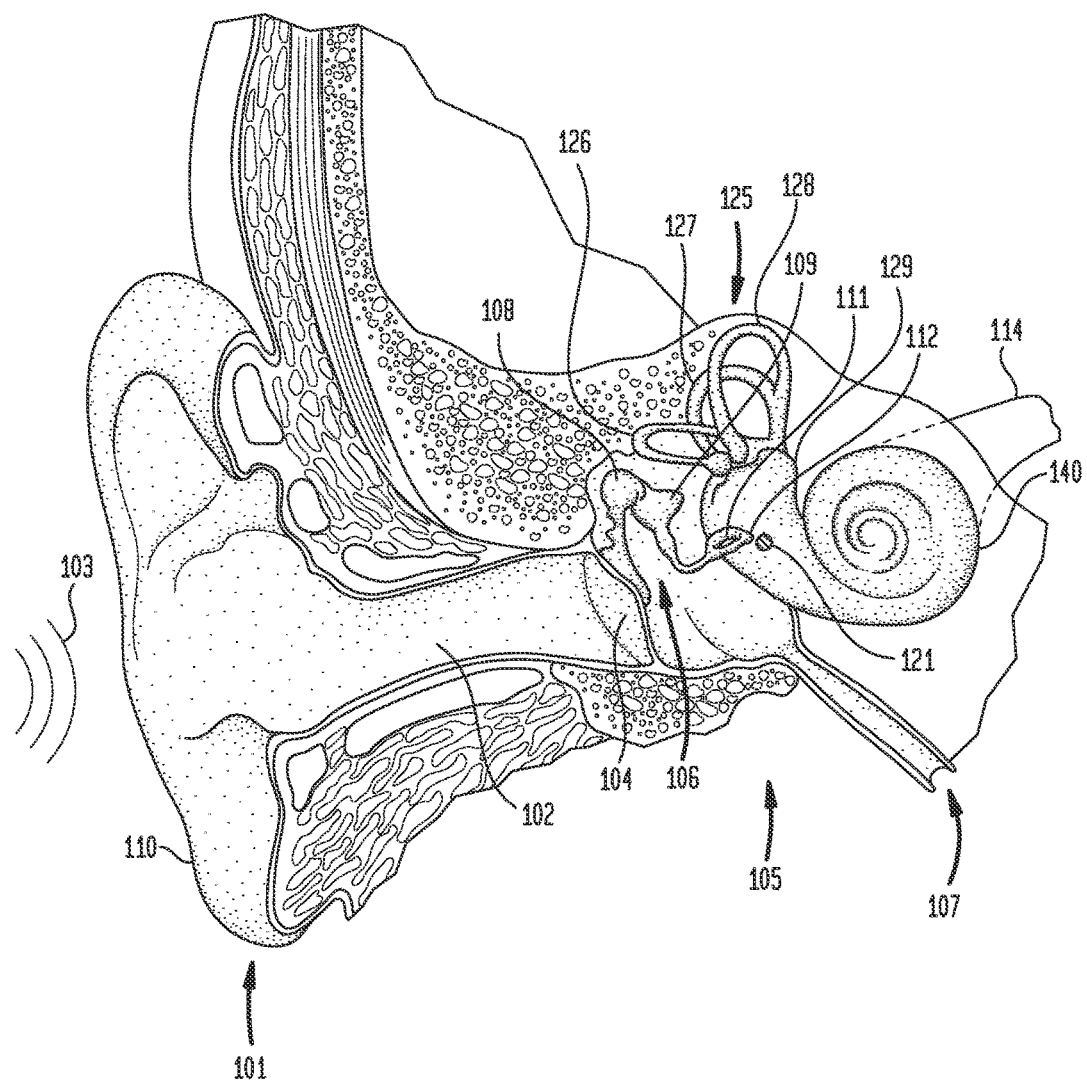
FIG. 1 is perspective view of a human ear.

FIG. 1 is perspective view of a human skull showing the anatomy of the human ear. As shown in FIG. 1, the human ear comprises an outer ear 101, a middle ear 105 and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window 112, which is adjacent to round window 121 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to the vibration of tympanic membrane 104. This vibration sets up waves of fluid motion of the perilymph within cochlea 140. Such fluid motion, in turn, activates hair cells (not shown) inside cochlea 140. Activation of the hair cells causes nerve impulses to be generated and transferred through the spiral ganglion cells (not shown) and auditory nerve 114 to the brain (also not shown) where they cause a hearing percept.

Figure 2A:
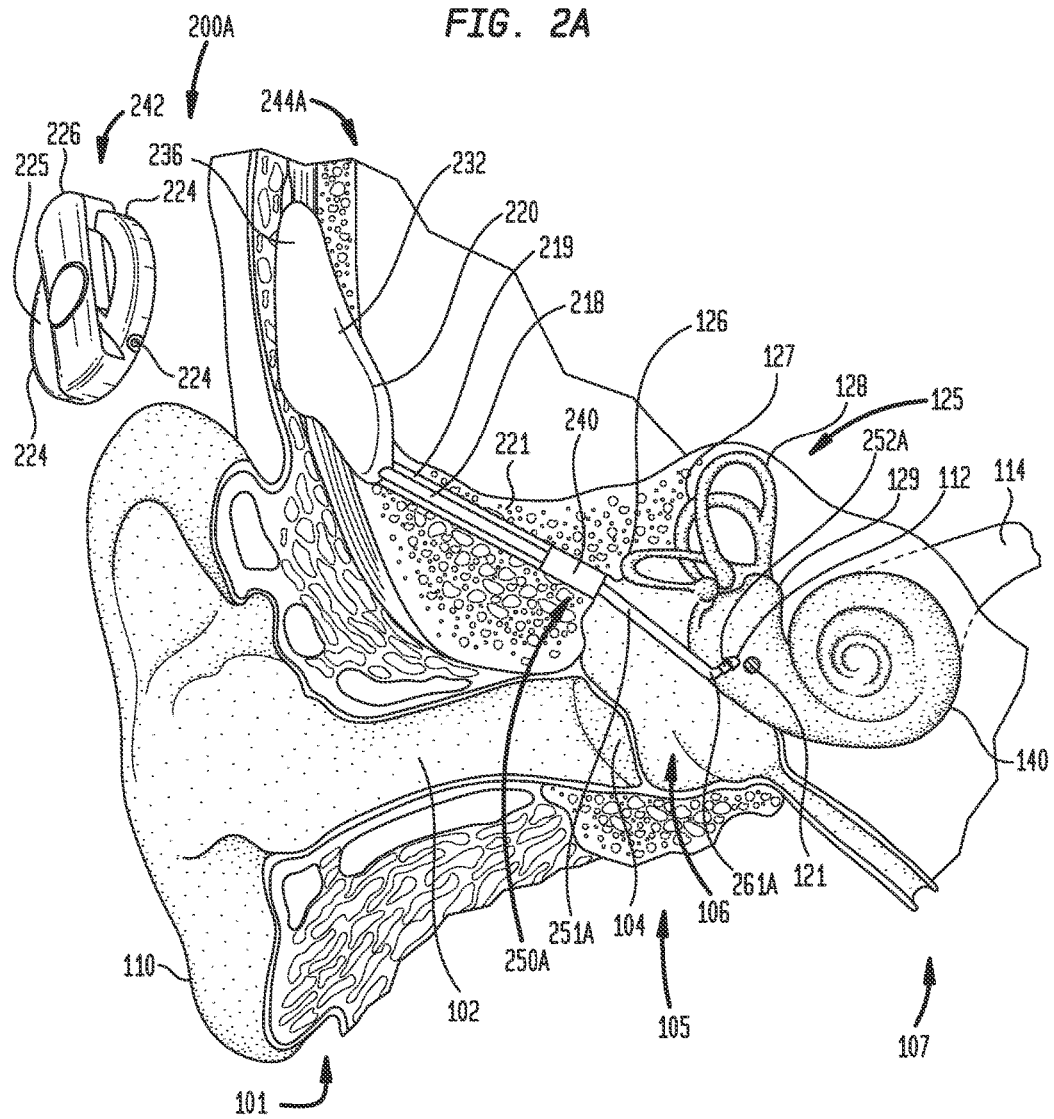
FIG. 2A is a perspective view of an exemplary Direct Acoustic Cochlear Implant (DACI), implanted in accordance with an embodiment.

FIG. 2A is a perspective view of an exemplary direct acoustic cochlear stimulator 200A in accordance with some exemplary embodiments. Direct acoustic cochlear stimulator 200A comprises an external component 242 that is directly or indirectly attached to the body of the recipient, and an internal component 244A that is temporarily or permanently implanted in the recipient. External component 242 typically comprises two or more sound input elements, such as microphones 224, for detecting sound, a sound processing unit 226, a power source (not shown), and an external transmitter unit 225. External transmitter unit 225 comprises an external coil (not shown). Sound processing unit 226 processes the output of microphones 224 and generates encoded data signals which are provided to external transmitter unit 225. For ease of illustration, sound processing unit 226 is shown detached from the recipient.

Internal component 244A comprises an internal receiver unit 232, a stimulator unit 220, and a stimulation arrangement 250A in electrical communication with stimulator unit 220 via cable 218 extending through artificial passageway 219 in mastoid bone 221. Internal receiver unit 232 and stimulator unit 220 are hermetically sealed within a biocompatible housing, and are sometimes collectively referred to as a stimulator/receiver unit.

Internal receiver unit 232 comprises an internal coil (not shown), a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated platinum or gold wire. The electrical insulation of the internal coil is provided by a flexible silicone molding (not shown). In use, implantable receiver unit 232 is positioned in a recess of the temporal bone adjacent auricle 110. It is noted that other embodiments may include a system in which some and/or all of the functionality of the external component 242 is included in the internal receiver unit 232 or other implanted component (e.g., microphones are implanted in the recipient). Such an exemplary alternate embodiment can be in the form of a so-called implantable hearing prosthesis. In such an embodiment, the external component 242 may not be present and/or may have different functionality.

In the illustrative embodiment of FIG. 2A, ossicles 106 have been removed. However, it should be appreciated that stimulation arrangement 250A can be implanted without disturbing ossicles 106, at least depending on the particular anatomy of a recipient.

Stimulation arrangement 250A comprises a transducer 240, a coupling rod 251A, and a coupling prosthesis 252A, which in this embodiment, coupling rod 251A includes an artificial incus 261A. The coupling rod 251A is connected to the coupling prosthesis 252A, although embodiments where coupling prosthesis is not present. Transducer 240 is fixed to mastoid bone 221 via a fixation system (not explicitly shown in the FIGs.).

In this embodiment, stimulation arrangement 250A is implanted and/or configured such that at least a portion of coupling rod 251A is located in the middle ear cavity and a portion of coupling prosthesis 252A (or other coupling, if present) abuts an opening in the vestibule 129.

As noted above, a sound signal is received by microphone(s) 224, processed by sound processing unit 226, and transmitted as encoded data signals to internal receiver 232. Based on these received signals, stimulator unit 220 generates drive signals which cause actuation of transducer 240. The mechanical motion of transducer 240 is transferred to coupling element 252A such that a wave of fluid motion is generated in vestibule 129. The wave of fluid motion continues into cochlea 140, thereby activating the hair cells of the organ of Corti. Activation of the hair cells causes appropriate nerve impulses to be generated and transferred through the spiral ganglion cells (not shown) and auditory nerve 114 to cause a hearing percept in the brain.

Figure 2B:
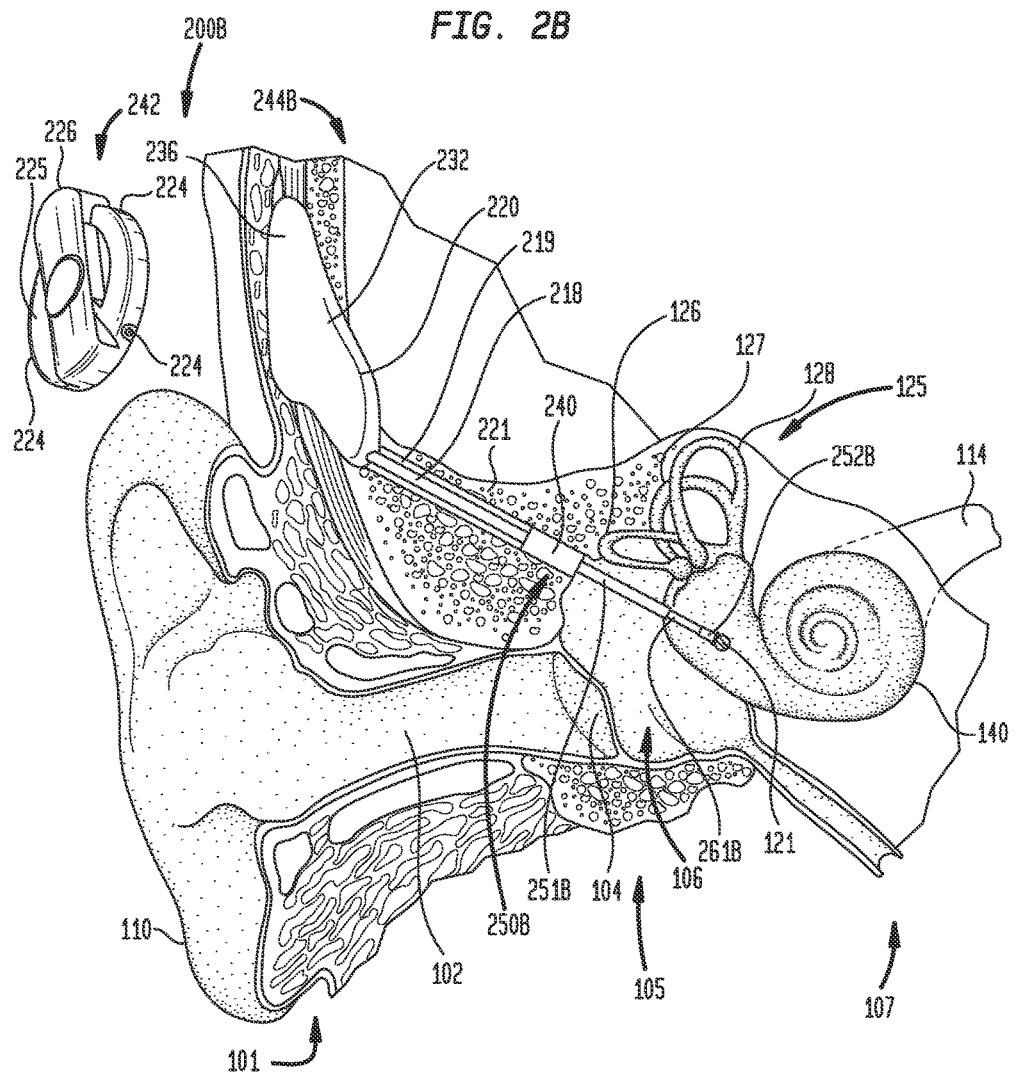
FIG. 2B is a perspective view of an exemplary Direct Acoustic Cochlear Implant (DACI), implanted in accordance with an embodiment.

FIG. 2B is a perspective view of another type of direct acoustic cochlear stimulator 200B in accordance with some exemplary embodiments. Direct acoustic cochlear stimulator 200B comprises external component 242 and an internal component 244B.

Stimulation arrangement 250B comprises transducer 240, optionally, a coupling element 252B (such as a stapes prosthesis) and a coupling rod 251B which includes artificial incus 261B which couples the transducer to the coupling element 252B. In this embodiment, stimulation arrangement 250B is implanted and/or configured such that at least a portion of coupling rod 251B is located in the middle ear cavity and a portion of coupling element 252B abuts and/or penetrates round window 121 or oval window 112 of cochlea 140. The mechanical motion of transducer 240 is transferred to coupling element 252B such that a wave of fluid motion is generated in the vestibulum 129. The fluid motion continues into cochlea 140, thereby activating the hair cells of the organ of Corti.

The embodiments of FIGS. 2A and 2B are exemplary embodiments of a Direct Acoustic Cochlear Implant (DACI) that provide mechanical stimulation directly to cochlea 140. Direct Acoustic Cochlear Implants (DACIs) directly provide mechanical stimulation to cochlea 140, for example via oval window 112 or round window 121 or any other opening in vestibule 129. FIG. 2C depicts an exemplary embodiment of a middle ear implant 200C having a stimulation arrangement 250C comprising transducer 240 and a coupling rod 251C. Middle ear implants provide mechanical stimulation to ossicles 106 in middle ear 105. For example, middle ear implants can provide mechanical stimulation to one of ossicles 106, such to incus 109 or stapes 111. Coupling rod 251C includes a coupling prosthesis 252C and an artificial incus 261C which couples the transducer to the coupling prosthesis 252C. In this embodiment, prosthesis 252C couples to stapes 111.

Figure 3:
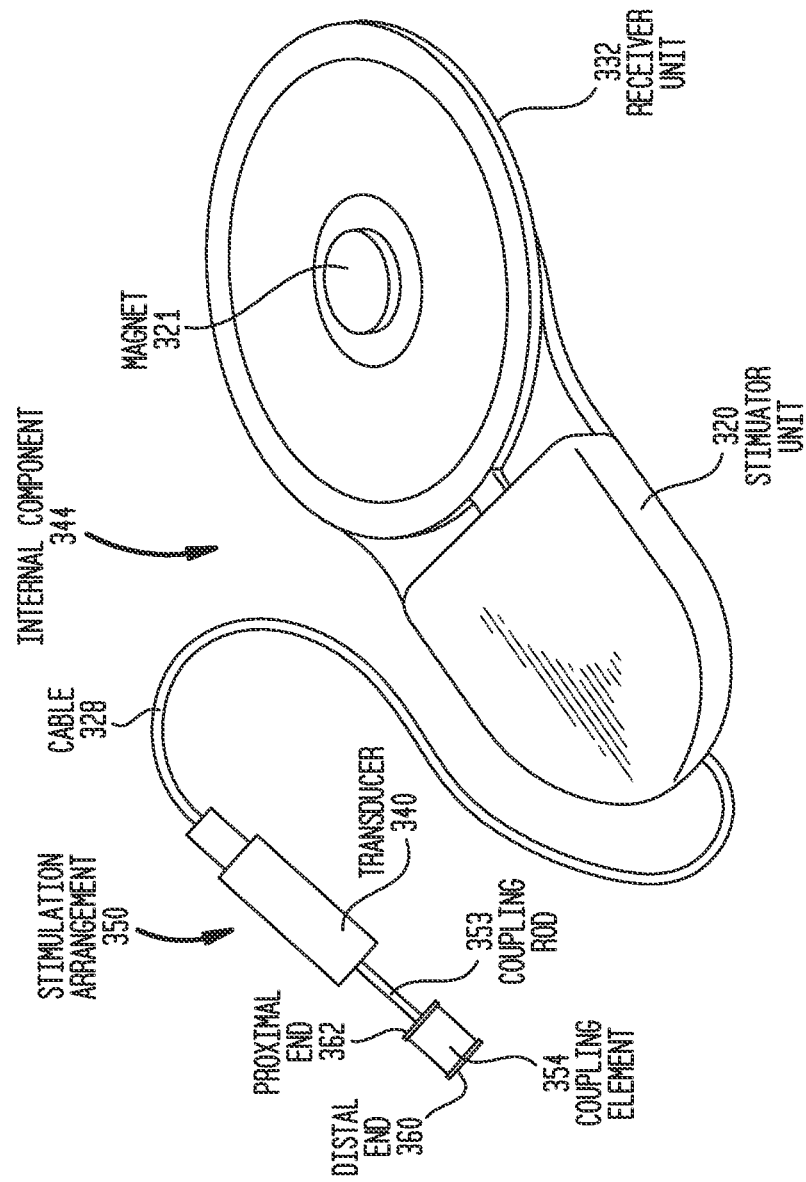
FIG. 3 is a schematic depicting an exemplary implantable component in accordance with an embodiment.

FIG. 3 is a perspective view of an exemplary internal component 344 of an implant which generally represents internal components 244 described above. Internal component 344 comprises an internal receiver unit 332, a stimulator unit 320, and a stimulation arrangement 350. As shown, receiver unit 332 comprises an internal coil (not shown), and a magnet 320, which, in some embodiments, can be fixed relative to the internal coil. Internal receiver unit 332 and stimulator unit 320 are typically hermetically sealed within a biocompatible housing. This housing has been omitted from FIG. 3 for ease of illustration.

Stimulator unit 320 is connected to stimulation arrangement 350 via a cable 328. Stimulation arrangement 350 comprises a transducer 340 with a coupling rod 353. A distal end 360 of coupling element 354 is configured to be positioned in one or more of the configurations noted above with respect to FIGS. 2A-2C. A proximal end of coupling element 354 is connected to transducer 340 via coupling rod 353 and the distal end of the prosthesis is directly coupled to the cochlea. In some embodiments, an artificial incus is attached to coupling rod 353 and coupled to the cochlea via coupling element 354. In operation, transducer 340 vibrates coupling element 354. The vibration of coupling element 354 generates waves of fluid motion of the perilymph, thereby activating the hair cells of the organ of Corti. Activation of the hair cells causes appropriate nerve impulses to be generated and transferred through the spiral ganglion cells and auditory nerve 114.

Some embodiments of methods and systems and devices for intra- and post-operative evaluation of a hearing prosthesis, such as a Direct Acoustic Cochlear Implant (DACI) or middle ear implant according to those detailed above and/or variations thereof, will now be described. It is noted that some embodiments of these are directed to other types of prostheses. In an exemplary embodiment, the devices, systems and/or methods detailed herein and/or variations thereof are applicable to any type of prosthesis that generates noise/sound, or other types of vibrations, providing that the teachings detailed herein and/or variations thereof may be practiced with such prosthesis. It is further noted that unless otherwise noted, the phrase "hearing prosthesis" as used herein includes any prosthesis that has utilitarian value with respect to the auditory system, such as, by way of example, a prosthesis that has utilitarian value associated with balance and/or tinnitus.

A high-level exemplary method will now be initially detailed to provide context for the more detailed embodiments introduced below. In this regard, FIG. 4 represents a flowchart for an exemplary method 400 according to an exemplary embodiment. Method 400 assumes that the hearing prosthesis has already been implanted into a recipient. Accordingly, in some embodiments, while not reflected in FIG. 4, method 400 can entail obtaining access to a recipient in which a hearing prosthesis has been implanted, which can include obtaining access during an operation or other surgical procedure associated with implantation of the hearing prosthesis. At method action 410, the implanted hearing prosthesis is operated. In an exemplary embodiment in which the implanted hearing prosthesis is at least part of a Direct Acoustic Cochlear Implant (DACI) or other middle ear implant, such as by way of example the middle ear implant internal component 344 of FIG. 3, the middle ear implant can be provided with a middle ear implant stimulus signal. By way of example, this can correspond to an acoustical signal in the form of sound travelling through air to a microphone of the prosthesis, a signal (e.g., inductance signal, etc.) provided to the receiver unit 332, a signal (electrical, optical, etc.) provided directly to a sound processor of the Direct Acoustic Cochlear Implant (DACI) or middle ear implant, a signal (electrical, optical, etc.) provided directly to a transducer of the middle ear implant, etc. Any device, system and/or method that will enable the implanted hearing prosthesis to be operated in a sufficient manner to practice at least some of the embodiments detailed herein and/or variations thereof can be used in at least some embodiments.

With continuing reference to FIG. 4, method action 420 includes capturing sound generated by a transducer of the hearing prosthesis during operation of the hearing prosthesis, such as, for example, that generated by transducer 340. In an exemplary embodiment, the action of capturing the generated sound is executed via the use of an earplug having an occluding feature and a sound capture device, where the earplug is located in the outer ear (ear canal) 102 according to an exemplary embodiment that will be detailed below.

It is noted that while the embodiments detailed herein are generally discussed in terms of sound/noise generation and sound/noise capture, other embodiments of the devices, systems and/or methods detailed herein and/or variations thereof can be utilized with other types of vibration generation and vibration capture. In this regard, an exemplary embodiment corresponds to at least some of the teachings detailed herein, where the terms sound and/or noise, etc., are replaced by the term vibration.

Having captured the sound (or other vibration(s)) generated by the transducer, method 400 proceeds to action 430, which entails comparing the captured sound to a sound model (details of the sound model are provided below). While not explicitly included in method 400, as will be detailed below, an exemplary embodiment includes a method in which, based on the comparison made at method action 430, the position of the transducer in the recipient (e.g., the position within artificial passageway 219) is adjusted based on the comparison.

Some embodiments of apparatuses that can be utilized to execute at least some of method 400 will now be described, followed by additional details of methods according to some embodiments.

Figure 5A:
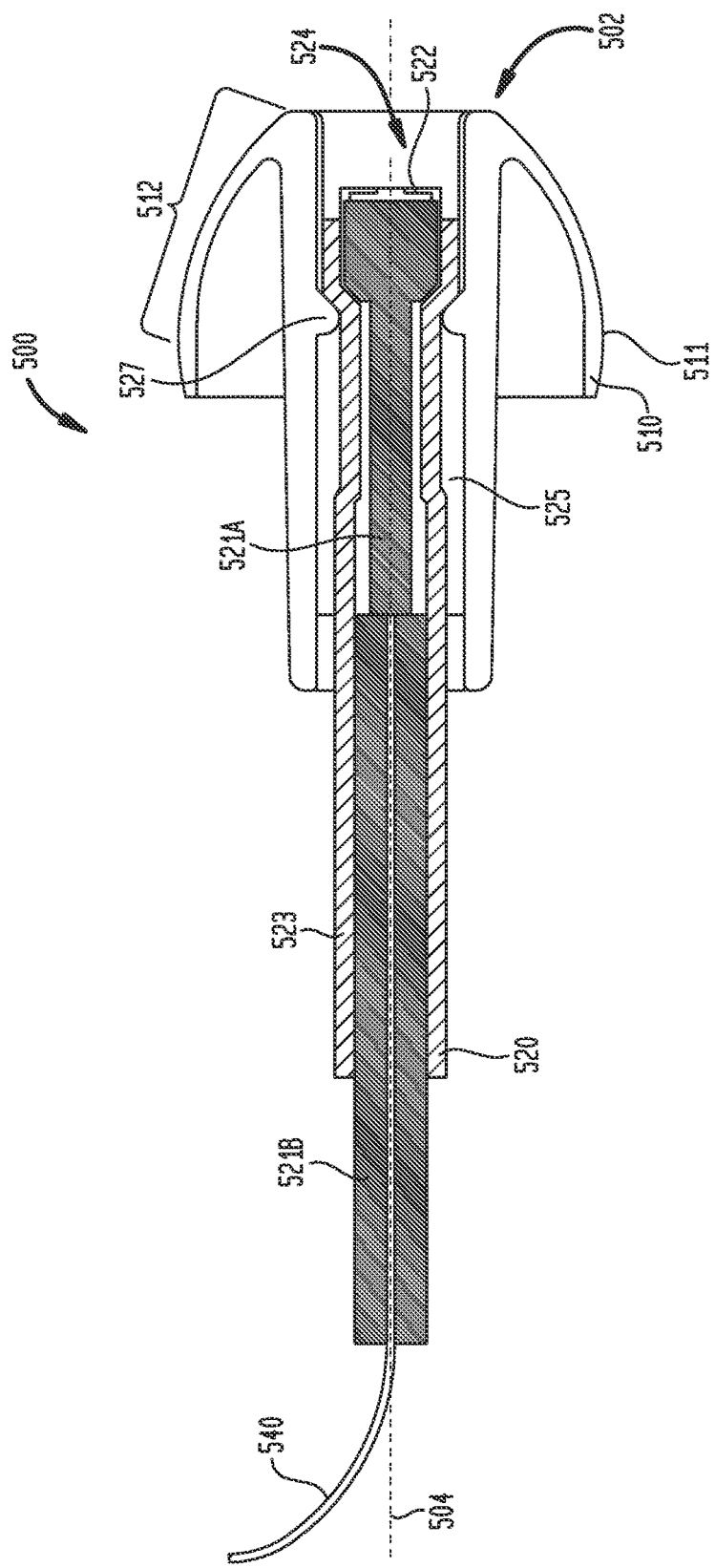
FIG. 5A depicts an exemplary earplug in accordance with an embodiment.

FIG. 5A depicts an exemplary earplug 500 according to an exemplary embodiment, which, in some embodiments, is part of a hearing prosthesis evaluation system, as will be described in greater detail below. As can be seen, earplug 500 includes an occluding apparatus 510 configured to occlude an ear canal 102 of a recipient. Supported by the occluding apparatus is a sound capture apparatus 520 which is integrated with the occluding apparatus 510.

Figure 5B:
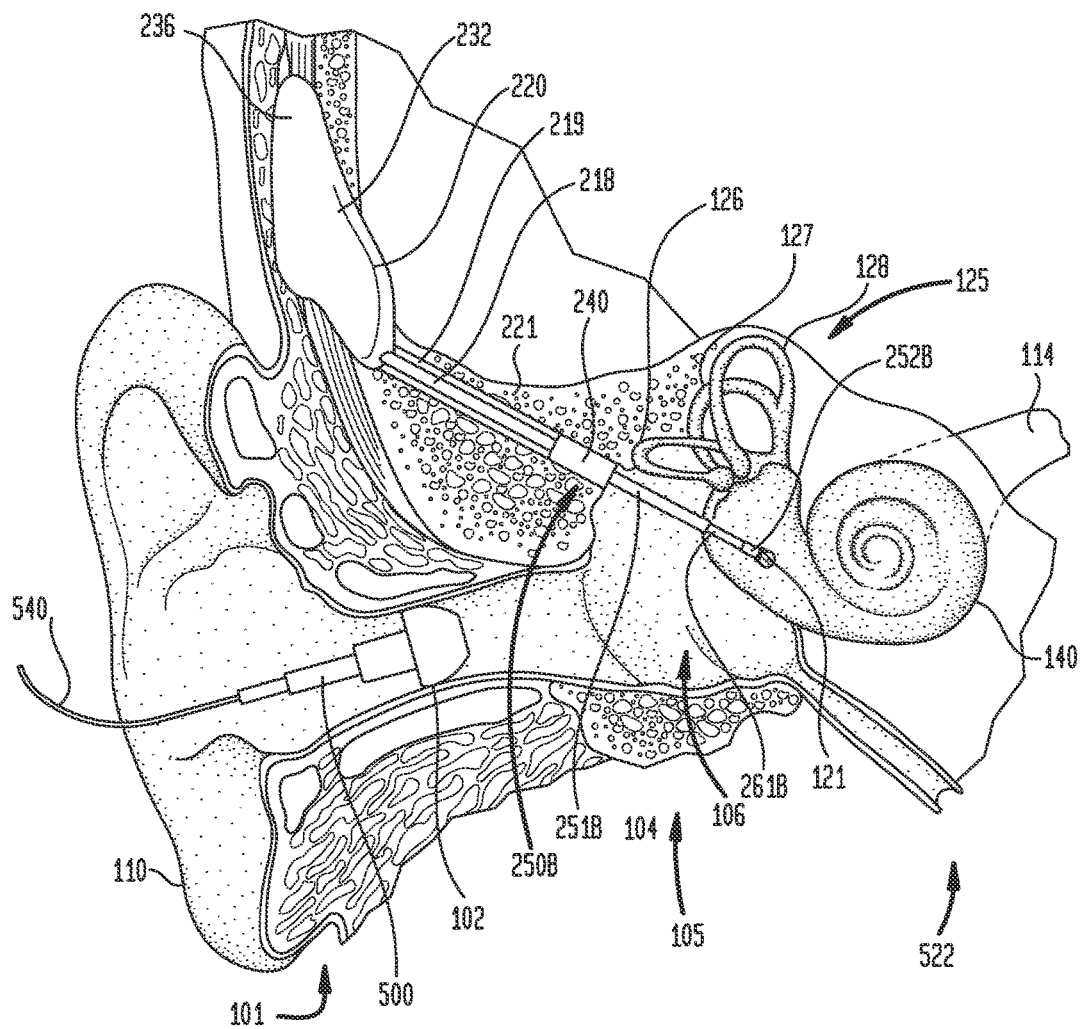
FIG. 5B depicts utilization of the earplug of FIG. 5A.

The sound capture apparatus 520, which may be a microphone, includes a sound receiver 522 that faces the middle ear when the earplug 500 is effectively positioned in the ear canal (in an exemplary embodiment, the sound receiver 522 includes a vibrating diaphragm that faces the middle ear), as is depicted by way of example in FIG. 5B. In this regard, FIG. 5B is an excerpt of FIG. 2B above, with the earplug 500 effectively positioned in ear canal 102. As can be seen, the sound receiver 522 is positioned relative to the occluding apparatus 510 such that the sound receiver 522 faces the middle ear 105 of the recipient when the distal end 502 of the earplug faces the middle ear 105 of the recipient.

By way of example and not by way of limitation, at least some embodiments of the earplug 500 have utilitarian value in that they are configured to capture sound produced by an implantable hearing prosthesis, such as the transducer 240 depicted in FIG. 5B. As can be seen, sound generated by transducer 240 travels through the middle ear 105 and then into the ear canal 102 where the sound is captured by the sound capture device 520 of the earplug 500. In an exemplary embodiment, where the ear drum 104 has been raised, such as is the case in FIG. 5B, the sound is directly captured by the sound capture device 520. Note that sound that reflects off of a solid object in the middle ear prior to being captured by the sound capture device 520 falls within the scope of "directly captured." This as differentiated from the scenario where the generated sound impinges upon the intact ear drum 104, causing the ear drum 104 to vibrate, resulting in pressure waves being formed on the earplug side of the ear drum, such that the sound generated by the transducer 240 is indirectly captured by the sound capture device 520 of the earplug 500.

As can be seen from the figures, the earplug 500 in general, and the sound capture apparatus 520 in particular, is connected to leads 540, which can be in electrical or optical communication with the sound capture apparatus 520, and configured to transmit corresponding signals representative of the captured sound to another component, such as by way of example, a component that is part of the hearing prosthesis evaluation system of which the earplug is also a part. It is noted that in some embodiments, instead of leads, a sound tube/pipe or a vibration conduction device can be used to convey captured sound or vibrations indicative of the captured sound away from the earplug 500. Any device, system and or method that will enable communication between the earplug 500 and another component, such as another component of a hearing prosthesis evaluation system detailed below, that will enable the teachings detailed herein and/or variations thereof to be practiced, can be used in some embodiments.

As can be seen from FIG. 5B, the occluding apparatus 510 is configured to support the sound capture apparatus 520 in the ear canal 102 such that when the occluding apparatus 520 is effectively positioned in the ear canal 102, the sound capture apparatus 520 is spaced from the wall of ear canal 102. While other embodiments can differ, in an exemplary embodiment, the occluding apparatus 510 is configured to support the sound capture device 520 at least approximately concentric with the ear canal 102.

Additional features of the earplug 500 according to the exemplary embodiment of FIG. 5A-5B include the occluding apparatus 510 extending distally relative to a distal end 524 of the sound capture apparatus 520. In this regard, as can be seen in FIG. 5A, the occluding apparatus 510 has a generally mushroom shape with a hollow extension through the longitudinal axis 504 of the earplug 500 (with regard to the mushroom shape, a hollow extension parallel and concentric with the stem and extending through the stem and the cap), and the top (cap) of the mushroom shape extends distally past the distal end 524. The hollow extension is a cavity in which the sound capture apparatus 520 is located. As will be further understood from FIG. 5A, the occluding apparatus 510 also extends proximally relative to the distal end 524 of the sound capture apparatus. Note further that the configuration depicted in FIG. 5A is characterized as having a sound receiver 522 located at or proximate the distal end of the occluding apparatus (which corresponds to the distal end 502 of the earplug). While the configuration of FIG. 5A is depicted such that the sound capture apparatus 520 is directly exposed to the ambient environment, in an alternate embodiment, a membrane or other covering that enables sound to be transferred from one side thereof to the other side may cover the opening of the hollow extension (e.g., at the distal end 502 of the earplug).

Sound capture apparatus 520 includes a body 521A that includes or otherwise supports sound receiver 522. Body 521A is removably attached to body 521B, such as, by way of example, a screw thread system, although in other embodiments, the two bodies are at least generally permanently attached to one another. At least a portion of body 521B has utility in that it supports lead 540, which extends at least partially therethrough as may be seen in FIG. 5A. Such can have utility by preventing lead 540 from kinking or otherwise being damaged during placement of earplug 500 into the ear canal. Sound capture apparatus 520 includes shell 523 that is interposed between (i) bodies 521A and 521B and (ii) occluding apparatus 510. The bodies 521A and 521B are attached to shell 523. Shell 523 includes a slightly recessed area 525 that interfaces with protrusion 527 of the occluding apparatus 510, as may be seen. In an exemplary embodiment, protrusion 527 is an elastomeric material that is sized and dimensioned, with respect to its fully expanded state, relative to the shell 523, to form an interference fit between the occluding apparatus 510 and the shell 523 (and thus the sound capture apparatus 520), thereby holding the sound capture apparatus 520 therein. In some embodiments, the interference fit is such that the sound capture apparatus 520 may be relatively easily moved forward and backward relative to the occluding apparatus 510, at least along the extent of the recessed area 525, to adjust the position the sound receiver 522 relative to the distal end of the occluding apparatus. Such may have utility, by way of example, in establishing a more utilitarian position of the sound receiver 522 in the scenario where the location of the occluding apparatus 510 cannot be adjusted/can only be adjusted over a relatively small range of locations relative to the ear canal (because, for example, the occlusion functionality may not be as utilitarian as the other locations). In other embodiments, the interference fit generally secures the sound capture apparatus 520 to the occluding apparatus 510.

As can be seen from FIG. 5B, at least a substantial portion 512 of the outer surface 511 of the occluding apparatus 510 is tapered toward the middle ear 106 when the earplug 500 is located in the ear canal 102.

In the exemplary embodiment depicted in FIG. 5A, the earplug is configured such that the functionality of (i) the capture of sounds travelling through (including originating in) the middle ear and the capture of sounds resulting therefrom (e.g., due to vibration of an intact ear drum resulting from those sounds) and (ii) the occlusion of the ear canal to substantially/effectively reduce, if not substantially/effectively eliminate, ambient sounds (e.g., sounds originating from an operating room/sounds originating from outside of the recipient) from reaching the sound capture device can be obtained using a single integrated apparatus (i.e., the earplug 500). Further, in the exemplary embodiment depicted in FIG. 5A, the earplug is configured to achieve both of the aforementioned functionalities by inserting a single apparatus (i.e., earplug 500) in the ear canal. In this regard, in such an exemplary embodiment, the earplug 500 is configured such that removal and installation force applied to the earplug 500 at one of the occluding apparatus 510 and the sound capture device 520 that imparts movement thereto moves the other of the occluding apparatus and the sound capture device by substantially the same amount, at least in the absence of elastic deformation of some and/or all of the components of the earplug 500 and/or the ear canal 102. In some embodiments, the earplug 500 is configured such that removal and installation force applied to the earplug 500 at one of the occluding apparatus 510 and the sound capture device 520 that imparts movement thereto moves the other of the occluding apparatus and the sound capture device by substantially the same amount, the amount being measured after substantially all (including all) elastic deformation that occurs during the movement has been reversed.

In an exemplary embodiment, the earplug 500 can be sterilized prior to insertion into the ear canal 102. Such sterilization can be done in relatively close temporal proximity to insertion (e.g., in a temporal manner akin to the sterilization of devices that are reused in a hospital) and/or in relatively distant temporal proximity to insertion into (e.g., in a temporal manner akin to the sterilization of devices at the manufacturer thereof prior to delivery to and storage at a hospital). In this regard, in some exemplary embodiments, at least substantially all outer surfaces of the occluding apparatus are made entirely out of or substantially entirely out of one or more materials that are sterilizable, such as, by way of example and not by way of limitation, silicone or other similarly sterilizable materials.

Exemplary sterilization procedures for sterilizing at least the outer surfaces of the earplug 500 include gamma ray sterilization, autoclave sterilization, and Ethylene Oxide (EtO) sterilization, such that the sound capture apparatus 520 remains functional/operational for use as detailed herein and/or variations thereof after sterilization. Accordingly, in some embodiments, at least substantially all outer surfaces and/or substantially all components of the earplug 500 are made entirely or substantially entirely out of materials that are sterilizable by one or more or all of the aforementioned processes.

As noted above, earplug 500 can be used when executing method action 420 above to capture the sound generated by a transducer of an implanted hearing prosthesis during operation of the hearing prosthesis (both during the implantation surgery/procedure and post-implantation/post-operatively (e.g., during a fitting session in a clinic or at home, hours, days, weeks, months or years after the procedure)). Thus, the earplug 500, can be used in vivo. Earplug 500 can also be used pre-implantation. Such can be the case if a test bed mimicking the outer and middle ear of a human (with and/or without mimicking the presence of an intact ear drum, as some uses of the earplug 500 and the other teachings detailed herein are associated with use on a ruptured, removed, not present, and/or flapped ear drum) is utilized, although in other embodiments, a test bed may not be utilized providing that sufficient sound from the transducer can be captured. The sound captured during method action 420 can be, in some embodiments, the sound of a moving component of the transducer 340 that moves when the transducer is stimulated. For example, such a component can be a diaphragm of the transducer that is used, for example, to hermetically seal the interior of the transducer 340 on the side of the transducer at which the coupling rod 353 is located. In an exemplary embodiment of a transducer 340, the diaphragm can be a relatively thin titanium disk, having a thickness of between about 5 to 50 micrometers. The coupling rod 353 can extend through the center of the diaphragm. Stimulation of the transducer results in movement of the coupling rod 353 and thus movement of the diaphragm (e.g., vibration of the diaphragm), at least in embodiments in which the diaphragm is mechanically linked to the coupling rod 353. This movement of the diaphragm creates sound. It is this sound that some embodiments of the earplug 500 can be used to capture, although it is noted that method 400 can be practiced with a device different from earplug 500.

Figure 6:
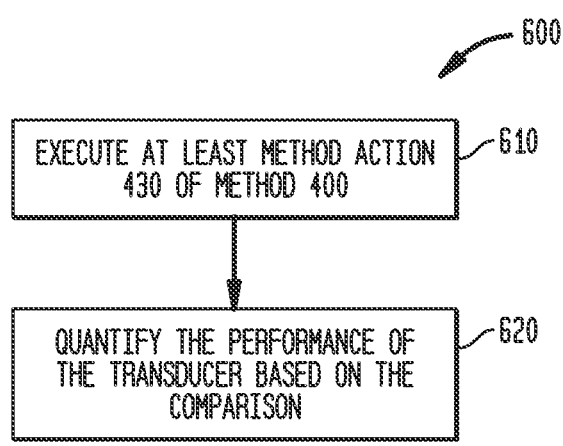
FIG. 6 is a flowchart for another exemplary method in accordance with an embodiment.

FIG. 6 represents a flowchart for an exemplary method 600 according to an exemplary embodiment. Method 600 starts with method action 610, which entails executing at least method action 430 (comparing the captured sound to a sound model) of method 400, although in other embodiments, some additional actions or all actions of method 400 are executed.

After method action 610 is executed, method action 620 is executed (with or without additional actions there between). Method action 620 entails quantifying performance of the transducer based on the comparison of action 610. In an exemplary embodiment, the quantification of the performance of the transducer based on the comparison is accomplished via a transfer function. By way of example, during the surgical implantation of the transducer 340, the ear drum 102 may be flapped, pierced, raised, removed, etc., although in other exemplary procedures, the ear drum may already be ruptured or not be present in the first instance. In this regard, the captured sound propagates from the transducer to the sound capture device through an opening in a boundary otherwise present due at least to the tympanic membrane.

Accordingly, a direct path between the transducer 340 and the sound capture device of the earplug 500 (or other device having the sound capture capabilities of the earplug 500) exists, and thus sound generated by the transducer (or other sound generated within the cavity of the mastoid bone and/or within the middle ear) will not encounter an impassible obstacle (e.g., an obstacle that the sound cannot travel around) at least until reaching the earplug 500. It should be appreciated that the presence of an air opening in the tympanic membrane is not utilized in some embodiments. For example, during post-operative measurements, the tympanic membrane will be intact in normal situations.

In an exemplary embodiment, the quantification of the performance of the transducer based on the comparison is performed without utilizing a reverse transfer function, such as, by way of example, through the measurement of another vibrating source (e.g., tympanic membrane) that vibrates due to the sound from the transducer striking the vibrating source, or the measurement of vibrations generated by the another vibrating source.

Figure 7:
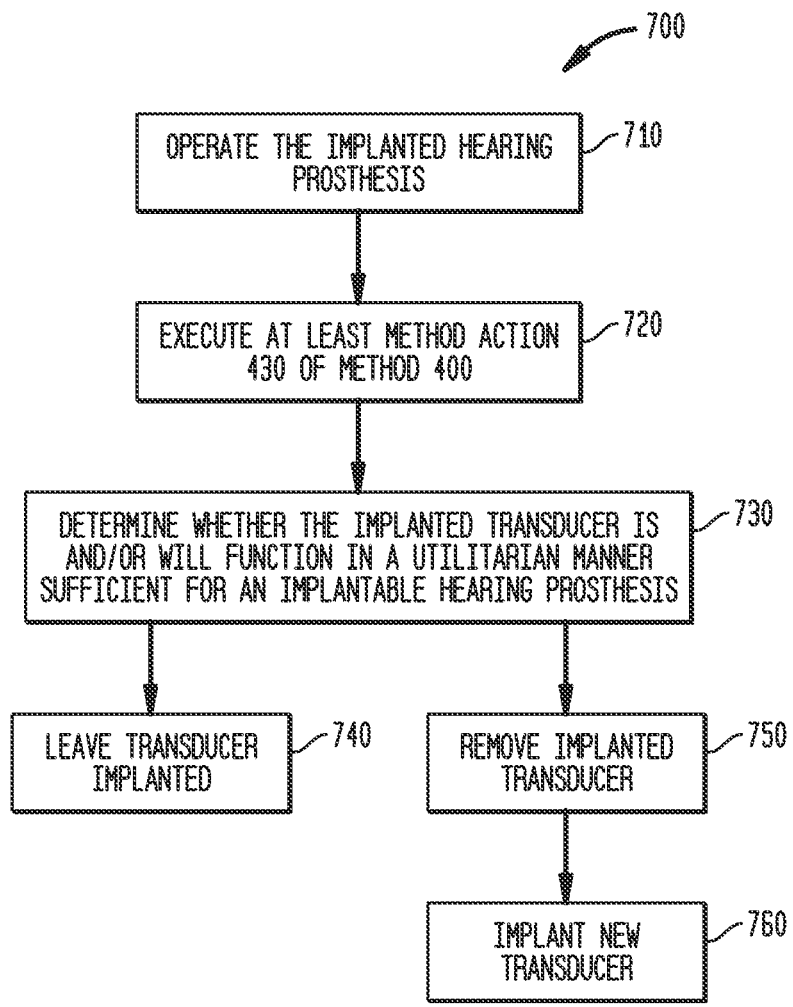
FIG. 7 is a flowchart for another exemplary method in accordance with an embodiment.

FIG. 7 represents a flowchart for an exemplary method 700 according to an exemplary embodiment. Method 700 starts with method action 710, which entails implanting a transducer of a hearing prosthesis, such as transducer 340, in a recipient. It is noted that method action 710 can be accomplished via a permanent or a temporary implantation of the transducer. After executing method action 710, which may or may not be preceded by additional actions not detailed herein, method action 720 is executed, which entails executing at least method action 430 (comparing the captured sound of the transducer to a sound model) of method 400. It is noted that method action 720 can include one or more or all additional actions of method 400.

At method action 730, a determination is made as to whether the implanted transducer is functioning and/or will function in a utilitarian manner sufficient for an implantable hearing prosthesis, based on the comparison of the captured sound of the transducer to a sound model. By way of example and not by way of limitation, the transducer can be damaged during and/or before implantation and/or the transducer can be improperly anchored/aligned, etc. The transducer can also become damaged and/or dislodged after implantation. One or more or all of these scenarios can result in the transducer not functioning in a utilitarian manner. Also, one or more or all of these scenarios can result in sound produced by the transducer during stimulation being different from that which would be produced by the transducer if the transducer was not damaged during and/or before implantation and/or the transducer was properly anchored/aligned, etc., respectively. This sound which would be produced by the transducer if the transducer was not damaged during and/or before implantation and/or the transducer was properly anchored/aligned, etc., corresponds to the sound of the sound model of action 430, as will be detailed below. Accordingly, based on the comparison of the sound produced by the transducer to that of the sound model (e.g., the sound which would be produced by the transducer if the transducer was not damaged during and/or before implantation and/or the transducer was properly anchored/aligned, etc.), the determination is made as to whether the implanted transducer is functioning and/or will function in a utilitarian manner sufficient for an implantable hearing prosthesis.

After executing method action 730, which may or may not be preceded by additional actions not detailed herein, based on the determination made at method action 730, method 730 either proceeds to method action 740 or method action 750. If a determination is made that the implanted transducer is functioning and/or will function in a utilitarian manner sufficient for an implantable hearing prosthesis, method action 740 is executed, which entails leaving the implanted transducer implanted (i.e., not removing the transducer from the recipient). If a determination is made that the implanted transducer is not functioning and/or will not function in a utilitarian manner sufficient for an implantable hearing prosthesis, method action 750 is executed, which entails removing the implanted transducer. Accordingly, method action 750 entails removing the implant from the recipient based on the comparison between the sound produced by the transducer and the sound model.

Method 700 includes an optional method action 760, which is optionally executed after method action 750 is executed. Method action 760 entails implanting a new implant (different implant from that removed) in the recipient. Because method action 760 is executed upon a determination that the implanted implant is not functioning and/or will not function in a utilitarian manner sufficient for an implantable hearing prosthesis, method action 760 entails implanting a new implantable hearing prosthesis in the recipient based on the comparison between the sound produced by the transducer and the sound model.

Figure 8:
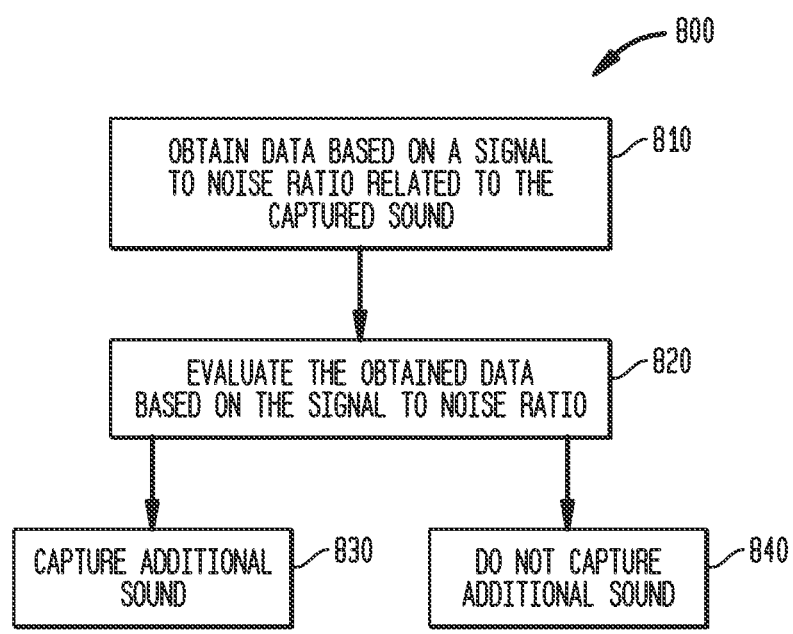
FIG. 8 is a flowchart for another exemplary method in accordance with an embodiment.
Figure 9:
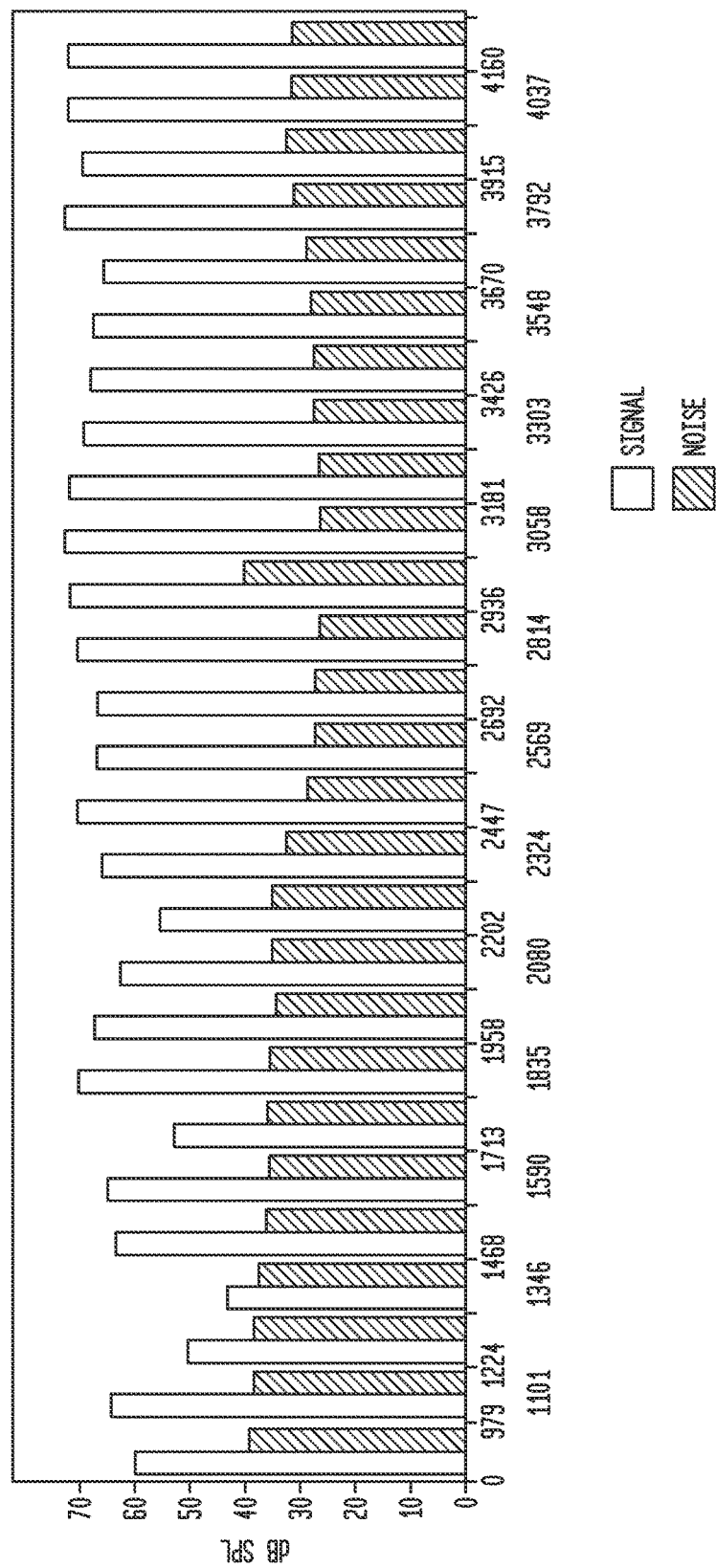
FIG. 9 depicts signal to noise ratio data in accordance with an embodiment.

An exemplary method includes evaluating a signal to noise ratio related to the sound captured in method action 420. In this regard. FIG. 8 presents method 800, which one or more or all method actions can be executed between method actions 420 and 430 of method 400. Method 800 includes method action 810, which entails obtaining data based on a signal to noise ratio related to the captured sound. The data based on signal to noise can comprise respective data for a plurality of signal to noise ratios for a plurality of respective frequency ranges. FIG. 9 presents an example of such data divided amongst various frequency ranges. Action 820 of method 800 entails evaluating the obtained data based on the signal to noise ratios. The evaluation can result in a determination that there is too much background noise associated with the captured sound and thus method action 830 should be executed, which entails capturing additional sound (e.g., method action 410 and 420 should be repeated). In such an eventuality, one or more or all of the methods detailed herein and/or variations thereof can include the action of repositioning the earplug 500 or corresponding apparatus to better occlude the ear canal, thereby reducing the amount of ambient noise that is captured by the sound capture apparatus of the earplug 500. Alternatively or in addition to this, the action of reducing the ambient noise can be executed, such as, by way of example, switching off machines in the proximity of the patients or during post-operative measurements, requiring healthcare professionals proximate the recipient to stop talking and/or moving while action 420 is executed.

The evaluation can result in a determination that any background noise associated with the captured sound is minor or relatively minimal and thus no additional sound needs to be captured (action 840 of method 800).

It is noted that the evaluation of action 820 can be automated. Alternatively or in addition to this, the evaluation can be performed by the surgeon or other healthcare professional based on the data (e.g., the surgeon can look at a graph akin to that depicted in FIG. 9, and extrapolate a generalized conclusion about whether or not there is too much background noise associated with the captured sound).

It is further noted that at least some and/or all devices, systems and/or methods detailed herein and/or variations thereof, and any components thereof (e.g., individual method actions) can be practiced/utilized before, during and after surgery and/or implantation procedures. In some embodiments, some and/or all method actions can be executed while the transducer is not coupled to, for example, the cochlea or one of the ossicles, etc.

Figure 10A:
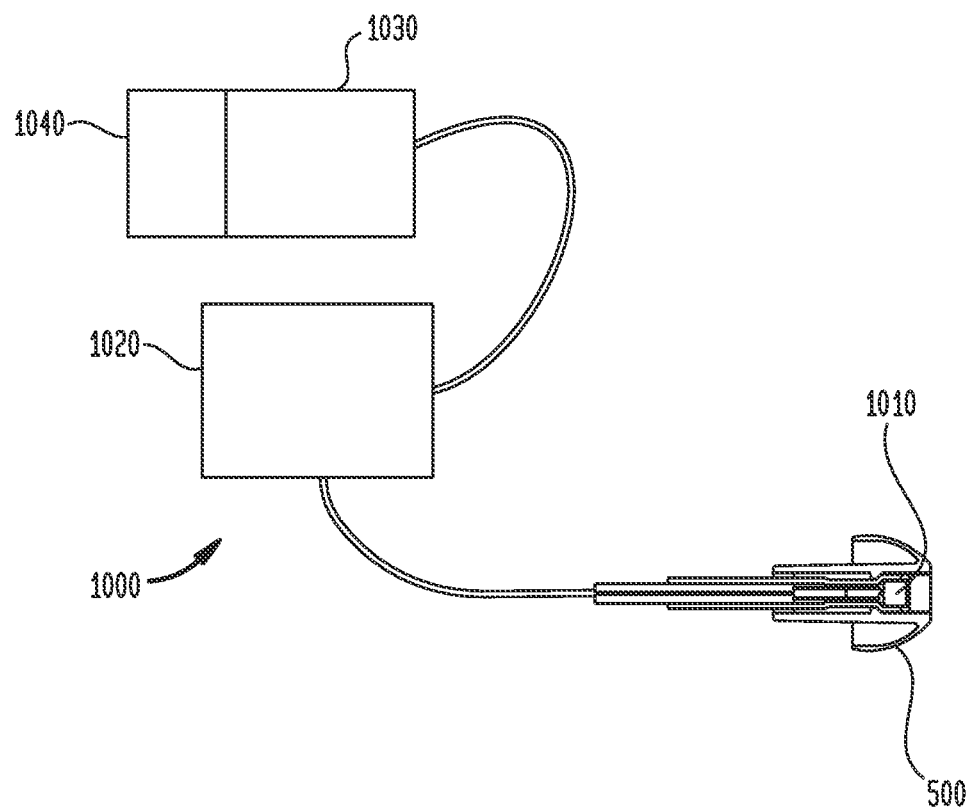
FIG. 10A is an exemplary system in accordance with an embodiment.

Some embodiments include devices and/or systems configured to execute one or more of all of the method actions detailed herein and/or variations thereof. FIG. 10 presents one such example with respect to system 1000. System 1000 is a system for evaluating an implanted hearing prosthesis, such as the transducer 340, having a vibrating diaphragm when in operation. As can be seen, system 1000 includes a sound capture apparatus 1010 configured to capture sound caused by the vibrating diaphragm that travels through a middle ear of a recipient, and to generate an audio signal representative of the captured sound. In an exemplary embodiment, sound capture apparatus 1010 can correspond to the sound capture apparatus 520 of earplug 500, as depicted in FIG. 10.

System 1000 can further include a controller 1020 configured to activate an implanted hearing prosthesis, such as to activate transducer 340, such that the hearing prosthesis generates sounds due to the activation. Controller 1020 can correspond to the external component 242, which, as noted above, can include a sound processor. While external component 242 is depicted herein as a so-called button sound processor, in other embodiments, external component 242 can be a so-called behind-the-ear (BTE) device to which an inductance coil has been attached. In this regard, such controllers can utilize inductance to control the implanted hearing prosthesis in a manner akin to how the external component 242 would control the prosthesis. That said, in other embodiments, the controller 1020 can control the prosthesis via electrical leads. Any device that can activate the implanted hearing prosthesis that is the subject of use of the system 1000 so as to implement the teachings herein and/or variations thereof can be used as the controller.

As can be seen from FIG. 10, the lead from the sound capture apparatus 1010 extends from the earplug 500 to the controller 1020. In this regard, controller 1020 both controls the prosthesis and receives input from the sound capture device 1010. Accordingly, the lead(s) from sound capture device 1010 can be fitted with an adapter so as to electrically interface with an input jack on controller 1030 (which can be an input jack on, for example, a BTE, which is used to supply an audio signal from, for example, a portable MP3 player or the like directly to the BTE).

The system 1000 can further include a sound analyzer 1030, which is in signal communication with controller 1020, and is configured to compare the audio signal from the sound capture device 1010 to a sound model (details of the sound model are provided below). In this regard, the sound analyzer can be a device configured to execute method action 430 of method 400. Lead(s) can extend between the controller 1020 and the sound analyzer 1030. Accordingly, the lead(s) can be fitted with an adapter so as to electrically interface with an output jack on controller 1030 (which can be an output jack on, for example, a BTE).

In an exemplary embodiment, the system 1000 is configured to capture and analyze sound directly produced by an implantable hearing prosthesis, although in other embodiments, the system 1000 can capture sound directly and indirectly.

Sound analyzer 1030 can be a computer, such as a personal computer or a mainframe computer, including software and/or firmware and/or any program product that enables the comparison of the audio signal from the sound capture apparatus to the sound model. While controller 1020 is depicted as a separate component from sound analyzer 1030, in an alternate exemplary embodiment, the controller 1020 and the sound analyzer 1030 can be an integrated component.

As noted above, an exemplary method includes evaluating data based on signal to noise ratios. Accordingly, in an exemplary embodiment, system 1000 includes a signal to noise ratio analyzer 1040 that is configured to execute at least method action 820 of method 800 as detailed above, such execution being done automatically. While signal to noise ratio analyzer 1040 is depicted as a separate component from sound analyzer 1030, in an alternate exemplary embodiment, the signal to noise ratio analyzer 1040 and the sound analyzer 1030 can be an integrated component (e.g. both can reside on the same computer via programming).

As detailed above, controller 1020 and sound analyzer 1030 can be an integrated component, and sound analyzer 1030 and noise ratio analyzer 1040 can be an integrated component. Thus, controller 1020, sound analyzer 1030 and noise ratio analyzer 1040 can be an integrated component. Accordingly, in embodiments where the controller 1020 corresponds to the external component 242 (e.g., a button sound processor or a BTE device, etc.), the external component 242 can have such functionality. Such a configuration can have utility in that it can enable a recipient of the external component 242 and a direct acoustic cochlear stimulator to independently initiate an evaluation of the stimulator, as will now be detailed.

FIG. 10B depicts an exemplary embodiment of an external component 1050 of a hearing prosthesis having such an integrated component embodied in a BTE device 1060 (an external component having the functionality of, for example, external component 242 detailed above) and also having the functionality of controller 1020, sound analyzer 1030 and noise ratio analyzer 1040 (although in some embodiments, the functionality of the sound analyzer 1030 and/or the noise ratio analyzer 1040 may not be present). It is noted that in an alternate embodiment, the integrated component can be embodied in a button sound processor or any other device that will enable the teachings detailed herein and/or variations thereof in general, and in particular the teachings detailed in the following paragraphs. More particularly, in some embodiments, external component 1050 corresponds to system 1000 as detailed above.

As can be seen in FIG. 10B, BTE device 1060 includes a lead 1070 that is connected to BTE device 1060. This lead leads to sound capture apparatus 1010 of earplug 500 which, as detailed above, is configured to capture sound caused by the vibrating diaphragm that travels through a middle ear of a recipient, and to generate an audio signal representative of the captured sound. It is noted that while the embodiment depicted in FIG. 10B shows lead 1070 connecting to the BTE device 1060 at the ear hook location, in other embodiments, the lead may be connected at another location. In this regard, the embodiment depicted in FIG. 10B takes advantage of existing BTE device designs where input from a microphone, such as a microphone from an in-the-ear (ITE) device or ear hook mounted microphone is inputted into the BTE device at this location (some additional details of such designs are detailed below with respect to FIG. 10D).

It is noted that in an exemplary embodiment, a recipient of the BTE device 1060 utilizes it in a manner that one utilizes such a device when part of a hearing prosthesis, owing to the fact that it can have the functionality of external component 242. Namely, it is used to enhance hearing. During such use, sound is captured by a device configured to capture ambient sound, such as through the use of an ITE device mounted microphone or an ear hook mounted microphone. However, the recipient can detach the microphone and attach earplug 500 to the BTE device 1060 to achieve the configuration of external component 1050 as depicted in FIG. 10B, thus, when the BTE device 1060 has the functionality of at least controller 1020, enabling the recipient to initiate evaluation of an implanted direct acoustic cochlear stimulator.

More particularly, FIG. 10C provides a flow chart for an exemplary method 1090 according to an embodiment of using external component 1050. At method action 1091, the recipient of BTE device 1060 (or a button sound processor having similar and/or the same functionality) and a direct acoustic cochlear stimulator utilizes the BTE device 1060 and the direct acoustic cochlear stimulator to enhance hearing. This can occur over a period (continuously or intermittently) of days, weeks, a month, six weeks, two months or more). At some point during or after this period, at method action 1092, the recipient attaches earplug 500 to the BTE device 1060 (which may require or otherwise be associated with the disconnection of a microphone used to capture ambient sound, if the same input jack is to be used). The earplug 500 may be stored at the recipient's home or the like, and attached to the BTE device 1060 when needed, and otherwise not used when not needed. Alternatively or in addition to this, the earplug 500 may be shipped to the recipient when needed (e.g., near the end or after the end of the aforementioned period of use of the BTE device to enhance hearing, and then shipped back to a location where it can be sterilized or the like for reuse.

At method action 1093, the earplug 500 is placed into the recipient's ear canal by the recipient. With the BTE device 1060 attached to the earplug 500, at method action 1094, the BTE device 1060 is activated to execute at least method actions 410 and 420 of method 400, or all of method 400. In this regard, operation of the implanted hearing prosthesis (action 410) occurs as a result of the BTE device 1060 controlling the implanted stimulator. Such activation may be activated directly by the recipient, or may be activated via a link to a remote location (e.g., via the internet or the like). In embodiments that execute method action 430 of method 400, method 1090 can include the action of providing an indication that the captured sound compares to the sound model in a manner indicative of a properly functioning actuator if such is the case (congruence between the captured sound and the sound model), and providing an indication that the captured sound compares to the sound model in a manner indicative of an improperly functioning actuator if such is the case (lack of congruence between the captured sound and the sound model). This indication may be provided to the recipient and/or to a location remote from the recipient and the external component.

It is noted that in some embodiments, method 1090 may include executing method 600 after executing one or more of the actions of method 400.

Figure 10D:
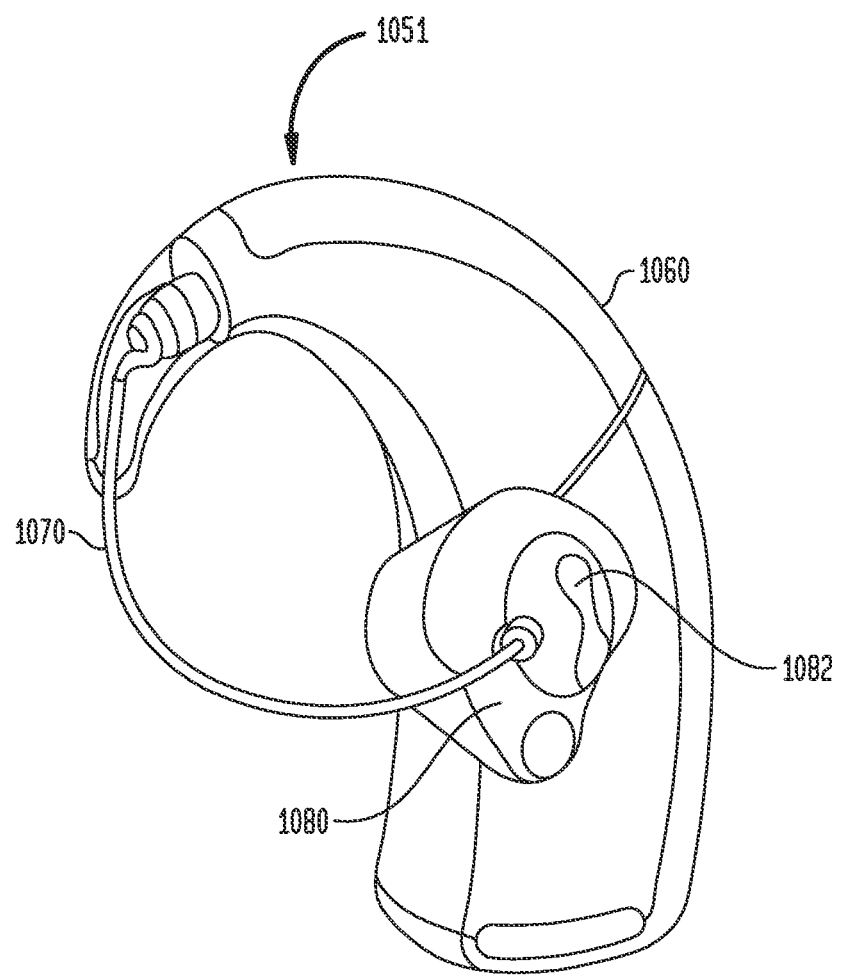
FIG. 10D is another embodiment of an external component of a hearing prosthesis in accordance with an exemplary embodiment.

FIG. 10D presents an alternate embodiment of an external component 1051, which has the functionality of external component 1050 detailed above. However, external component 1051 includes an ITE device 1080 connected to the BTE device 1060 via lead 1071. ITE device 1080 includes a microphone 1082 configured to capture ambient sound as is enabled by the art. However, ITE device 1080 is different from prior art ITE devices in that it also includes a sound capture apparatus (not shown) on the opposite side of the ITE device 1080 from microphone 1082. That is, instead of facing outward from the ear canal, the sound capture apparatus faces inward, towards the middle ear. In an exemplary embodiment, the sound capture apparatus of the ITE device has the functionality of the sound capture apparatus of earplug 500. In an exemplary embodiment, ITE device 1080 has the functionality of earplug 500.

The exemplary embodiment of FIG. 10D enables execution of some or all of method 400 (and some or all of method 600) via BTE device 1060 without attaching earplug 500 to the BTE device 1060. In an exemplary embodiment, the sound capture apparatus is normally not activated (e.g., such as when the microphone 1082 is used during hearing enhancement), but is activated when method 400 and/or method 600 is executed using the BTE device 1060.

As noted above, embodiments of external component 1050 (or 1051) are not limited to the use of BTE devices. In an exemplary embodiment, element 1060 can be a button sound processor. In such an exemplary embodiment, the earplug 500 (or ITE device 1080) may communicate wirelessly with button sound processor, although in other embodiments, communication may be executed wirelessly. Any device system and/or method that will enable the teachings detailed herein and/or variations thereof associated with enabling the recipient to partake in executing at least some actions of method 400 and/or some actions of method 600 may be utilized in some embodiments.

The exemplary embodiments of external components 1050 and 1051 detailed above have been described in terms of each having an analyzer corresponding to sound analyzer 1030, thus permitting method action 430 to be executed. However, in other embodiments, external components are configured to enable the captured sound to be transmitted to a location remote from the external component. This functionality may be a substitute for or an addendum to the functionality associated with sound analyzer 1030 (i.e., the sound analyzer 1030 may or may not be present in the external components). Such may have utility in a scenario where the transmitted captured sound is analyzed at a remote location. That is, instead of being analyzed by the external component, it is analyzed by a computer or audiologist or other device, system and/or method at a location remote from the recipient.

Some exemplary features of the sound model referenced above will now be described. In an exemplary embodiment, the sound model is a model of sound produced by an implanted transducer of an implanted hearing prosthesis, such as transducer 340. The sound model can be based on one or more variables. Indeed, in at least some exemplary embodiments, any variable(s) that will enable the devices, systems and/or methods detailed herein, including the comparisons detailed herein, and/or variations thereof, can be utilized.

In an exemplary embodiment, the sound model is a model based on an ideal output from the hearing prosthesis for a given transducer stimulation. The ideal output is an output for a properly functioning and/or implanted transducer (i.e., one that is not damaged and/or properly coupled/aligned, etc.). The ideal output can be based on empirical and/or computational data. Additional details associated with the development of the sound model and the variables upon which it can be based will now be described by way of example and not by way of limitation. In this regard, any data that will enable the development of the sound model can be data upon which the sound model is based.

The sound model can take into account dampening that may occur as a result of sound traveling from the transducer through the middle ear and/or through the outer ear ear canal, to the extent that the sound must travel there through, to the sound capture apparatus. Because the sound is directly captured owing to the folding, etc., of the ear drum, such dampening can be, in some models, only about 1, 2, 3, 4, 5, 6, 7, 8, 9, or 10 dB, or any range encompassing these values. Some sound models can disregard the dampening as such dampening can be nominal in view of other variables.

The sound model can be based on an ideal decibel level. In this regard, the sound capture device can output a signal indicative of the decibel level of the sound captured at the sound capture apparatus (this can be based on a voltage/amplitude varying signal, a frequency varying signal, etc., output from the sound capture apparatus), and this output can be compared to such a sound model. It is noted that the sound model based on an ideal decibel level can be a model that utilizes voltage level if voltage level is indicative of an ideal decibel level. That is, by way of example, output voltage from the sound capture device can be compared to a voltage level indicative of an ideal decibel level without converting the voltage(s) to the corresponding decibel levels.

The sound model can be based on an ideal output transfer curve. In this regard, the sound capture device can output a signal indicative of the intensity of the sound captured at the sound capture apparatus over a range of frequencies (FIG. 9 depicts the transducer output vs. frequency for such output, and this output can be compared to a sound model based on an ideal output transfer curve.

The sound model can be a parametric model. In this regard, the model may not be a "perfect" model, but instead can be based on different variables that approximate a properly functioning transducer.

In an exemplary embodiment, the sound model corresponds to an "acceptance band." In such an embodiment, comparison of the captured sound (output from the sound capture device) to the sound model can entail determining whether the output from the sound capture device falls within the acceptance band. Output that falls within the acceptance band is indicative of a properly functioning/properly anchored implanted transducer. Output that falls outside the acceptance band is indicative of a malfunctioning/improperly anchored implanted transducer.

Figure 11:
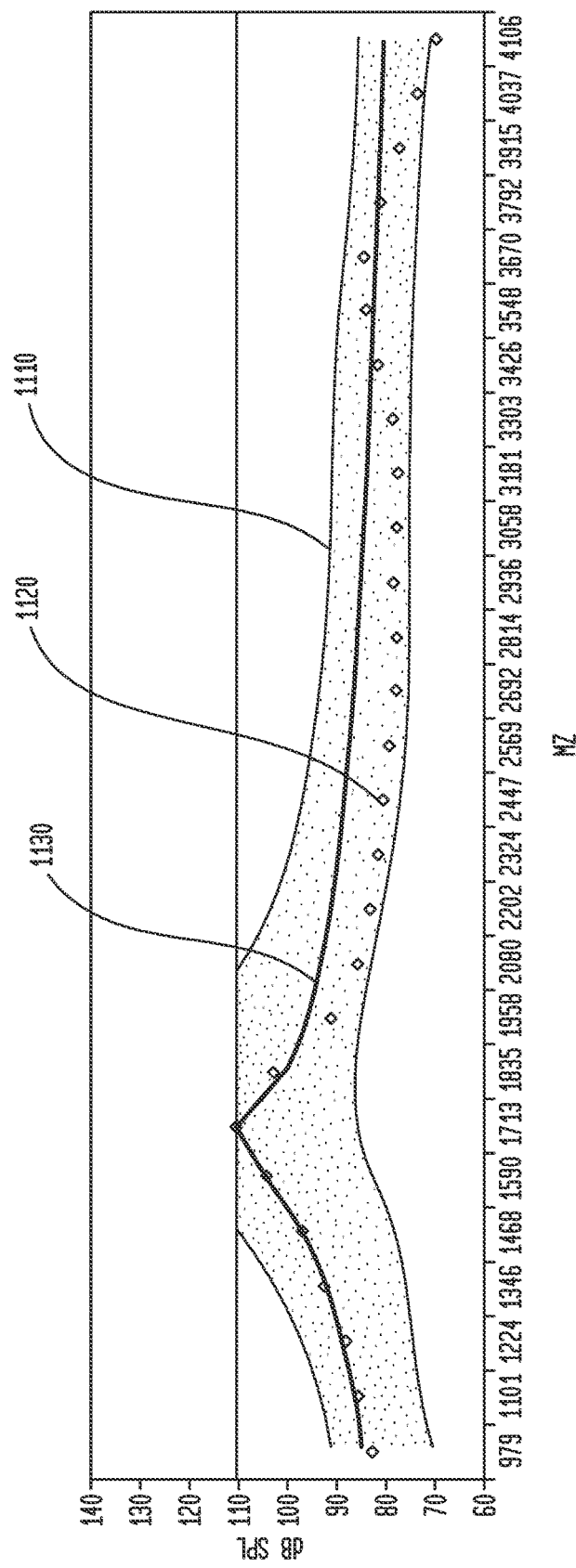
FIG. 11 depicts an exemplary acceptance band in accordance with an embodiment.

FIG. 11 depicts an exemplary acceptance band 1110 for various frequencies. FIG. 11 also depicts output values 1120 for various frequency bands, and a curve 1130 fit to those output values. As can be seen, curve 1130 falls within the acceptance band 1110. Accordingly, curve 1130 is indicative of a properly functioning/properly anchored implanted transducer.

Curve 1130 corresponds to a transfer function of the transducer. Because it is based on sound captured directly from the transducer, it is a direct transfer curve of the transducer (as opposed to a reverse transfer curve). In an exemplary embodiment, the direct transfer curve, and thus the transfer function, is a mathematical representation of the relationship between input and output of a given system in terms of frequency. In an exemplary embodiment, the given system is a hearing prosthesis. A relationship exists between the input of the hearing prosthesis and an output of the hearing prosthesis. This relationship is characterized for a given number of different frequency bands. By placing the measured values for each frequency band next to each other on a single graph in ascending order, a transfer curve is obtained.

In an exemplary embodiment, again where the observed system is the hearing prosthesis, the transfer function is a relationship that exists between the applied voltage (input of the hearing prosthesis) and the sound pressure level the device produces in response to that voltage (output of the hearing prosthesis), characterized for a certain amount of different frequency bands.

In an exemplary embodiment, system 1000 can be configured to deduce the transfer function, including the direct transfer function, of the implantable hearing prosthesis (e.g., transducer 340).

In an exemplary embodiment, the acceptance band 1110 (and thus the sound model), is based on variations of the output transfer function of different transducers. By way of example, such variations can be due to a varying resonance frequency of the transducer, damping associated with the coupling to the inner ear, a fitting constant or a mean deviation based on empirical data of the implanted transducer.

It is noted that some exemplary embodiments include adjusting the sound model from its original values, at least in some instances. In this regard, as detailed above, the sound model is a model based on an ideal output from the hearing prosthesis for a given transducer stimulation. However, the model may be refined or otherwise adjusted as a result of the acquisition of data or information beyond that on which the model is based (i.e., ideal output). By way of example, such data may be device or patient data, and may be acquired through a fitting procedure or the like. Using this information, an adjusted sound model unique for a given recipient and/or implanted transducer can be developed, and can be utilized in subsequent evaluations of that particular recipient and/or transducer. For example, upon a determination that the transducer is functioning properly based on an initial comparison of captured sound to the sound model, the sound model may be adjusted based on the captured sound. That is, the captured sound will deviate somewhat from the sound model, but that deviation will be an acceptable deviation, and the sound model is adjusted accordingly. This adjusted sound model can subsequently be used to determine whether the implanted transducer has experienced a change in performance from the time that the sound model was adjusted. This as contrasted to comparing captured sound at a later date to the sound model based on the ideal output, which might only reveal that the captured sound is still within acceptable deviation of the sound model. Such can permit the customization of a sound model to a given recipient and/or transducer.

Alternatively and/or additionally, a scenario may exist where the comparison of the captured sound to the sound model is indicative of a transducer functioning in a less than desirable or optimal manner, but the recipient indicates sufficient functionality of the transducer. Instead of explanting the transducer, the captured sound may be utilized as a new sound model, or the sound model may be modified based on the captured sound, and the new or modified sound model can then be used in future evaluations and/or fitting routines.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A system for evaluating an implantable prosthesis having a vibrating component when in operation as a result of reception by the implantable prosthesis of a stimulus signal in the form of an RF signal that travels through skin of a recipient of the implantable prosthesis to reach the implantable prosthesis, comprising: a vibration capture apparatus configured to capture vibration caused by the vibrating component traveling through a middle ear of a recipient, and to generate a signal different from the RF signal that is representative of the captured vibration; and an analyzer configured to compare the signal to a vibration model.

2. The system of claim 1, wherein:
the prosthesis is a hearing prosthesis;
the vibrating component causes sound;
the vibration capture apparatus is a sound capture apparatus configured to capture sound caused by the vibrating component traveling through the middle ear of a recipient;
the signal is an audio signal representative of the captured sound;
the vibration model is a sound model; and
the analyzer is a sound analyzer configured to compare the audio signal to the sound model.

3. The system of claim 2, wherein:
the sound analyzer is a personal computer including a software program configured to compare the captured sound signal to the sound model.

4. The system of claim 2, wherein:
the sound model is a model of sound produced by an implanted transducer of the prosthesis.

5. The system of claim 4, wherein:
the implanted prosthesis comprises a transducer of one of a Direct Acoustic Cochlear Implant (DACI) and middle ear implant.

6. The system of claim 2, wherein the sound model is a parametric model.

7. The system of claim 2, wherein the system is configured to capture and analyze sound produced by an implanted prosthesis.

8. The system of claim 7, wherein:
the system is configured to capture and analyze sound directly produced by an implantable prosthesis.

9. The system of claim 2, wherein:
the system is configured to deduce a direct transfer function of an implantable prosthesis.

10. The system of claim 2, further comprising:
a controller configured to stimulate an implanted prosthesis such that the prosthesis generates sounds due to the stimulation.

11. The system of claim 10, wherein:
the implanted prosthesis is one of a Direct Acoustic Cochlear Implant (DACI) and middle ear implant.

12. The system of claim 2, further comprising:
a signal to noise ratio analyzer.

13. The system of claim 2, wherein:
the sound model is a model based on an ideal output transfer curve.

14. The system of claim 13, wherein:
the sound analyzer is configured to compare data based on the captured sound to a range of output levels along the frequency curve.

15. The system of claim 14, wherein:
the range of output levels are based on variations of one or more transducers due to the varying resonance frequency, damping, pressure, temperature, a fitting constant and a mean deviation from the average implant transfer function.

16. A method of evaluating an implanted prosthesis, comprising: operating the implanted prosthesis; capturing vibrations generated by a transducer of the prosthesis during said operation; comparing the captured vibration to a vibration model, wherein the vibrations travel from the transducer, through the recipient, to a vibration capture apparatus that captures the vibrations; and evaluating the performance of the implanted prosthesis based on the comparison, wherein the action of operating the implanted prosthesis includes providing the implanted prosthesis with a stimulus signal in the form of an RF signal that travels through skin of the recipient to reach the implanted prosthesis.

17. The method of claim 16, wherein:
the prosthesis is a hearing prosthesis;
the captured vibrations are captured sound; and
the vibration model is a sound model.

18. The method of claim 17, wherein:
the captured sound is sound generated by a diaphragm of the transducer.

19. The method of claim 17, wherein:
the captured sound is sound generated by stimulation of the transducer of one of a Direct Acoustic Cochlear Implant (DACI) or middle ear implant.

20. The method of claim 17, wherein:
the captured sound is sound directly propagating from the transducer.

21. The method of claim 17, further comprising:
quantifying performance of the transducer based on the comparison via a direct transfer function.

22. The method of claim 17, further comprising:
quantifying performance of the transducer based on the comparison without utilizing/recording a reverse transfer function.

23. The method of claim 17, further comprising:
implanting the transducer in the recipient; and
adjusting the position of the transducer in the recipient based on the comparison.

24. The method of claim 17, wherein:
the captured sound propagates from the transducer to a sound capture device that captures the sound through an opening in a boundary otherwise present due at least to the tympanic membrane.

25. The method of claim 17, further comprising:
implanting the transducer in the recipient;
removing the transducer from the recipient based on the comparison; and
implanting a new transducer in the recipient based on the comparison.

26. The method of claim 17, further comprising:
obtaining data based on a signal to noise ratio related to the captured sound;
evaluating the data based on the signal to noise ratio; and
capturing additional sound generated by the transducer during a subsequent operation from the operation that generated the captured sound based on the evaluation of the data based on the signal to noise ratio.

27. The method of claim 26, wherein:
the signal to noise ratio comprises a plurality of signal to noise ratios for a plurality of frequency ranges.

28. The system of claim 1, wherein:
the analyzer is part of an external component of the implantable hearing prosthesis.

29. The system of claim 28, wherein:
the analyzer is part of a BTE device or a button sound processor.

30. A hearing prosthesis, comprising:
a control system configured to activate an implantable device having a vibrating component that vibrates when in operation;
a sound capture apparatus configured to capture ambient sound originating from a source external to the recipient;
the vibratory component;
a sound processor, wherein the hearing prosthesis is configured such that the sound processor processes signals outputted by the sound capture apparatus in response to the captured ambient sound and is configured to generate a signal provided based on the processing to be provided to the vibratory component to cause the vibratory component to vibrate to evoke a hearing percept due to the vibration of the vibratory component; and
a vibration capture apparatus separate from the sound capture apparatus configured to capture vibration caused by the vibrating component traveling through a recipient, and to generate a signal representative of the captured vibration.

31. The hearing prosthesis of claim 30, further comprising:
a BTE device or a button sound processor, wherein the control system, the sound capture apparatus and the sound processor is part of the BTE device or the button sound processor, respectively, and the vibration capture apparatus is in electronic communication with BTE device or the button sound processor, respectively.

32. The hearing prosthesis of claim 30, further comprising:
an analyzer configured to compare the signal to a vibration model.

33. The hearing prosthesis of claim 30, wherein:
the hearing prosthesis is configured to transmit the generated signal representative of the captured sound to a location remote from the hearing prosthesis.

34. The hearing prosthesis of claim 32, wherein:
the hearing prosthesis is configured to provide a recipient an indication of at least one of:
congruence between the signal and the vibration model; or
lack of congruence between the signal and the vibration model.

35. The system of claim 1, wherein:
the vibration model is a model of vibration produced by the vibrating component.

36. The system of claim 35, wherein:
the vibration model addresses dampening resulting from vibrational travel from the vibrating component to the vibration capture apparatus.

37. The system of claim 35, wherein:
the vibration model is based on at least one of an ideal decibel level or an ideal output transfer curve.

38. The system of claim 1, wherein:
the vibration model is a parametric model.

39. The system of claim 1, wherein:
the vibration model corresponds to an acceptance band.

40. The method of claim 16, wherein:
the evaluated implanted prosthesis is implanted in a person without natural hearing.

41. The hearing prosthesis of claim 30, wherein:
the hearing prosthesis is configured such that the vibration capture apparatus is removable from the hearing prosthesis, and the hearing prosthesis is configured to evoke a hearing percept in the absence of the vibration capture apparatus.

42. The system of claim 1, wherein:
the analyzer is configured to compare the signal to the vibration module utilizing at least one of software or firmware.

43. The method of claim 17, wherein:
the operation of the prosthesis results in components of the transducer moving relative to one another such that sound is produced by those components that is delta to output of the prosthesis that is used to impart a hearing percept, wherein the components moving relative to one another generate the vibration which corresponds to the captured sound.

44. The method of claim 17, wherein:
the implanted prosthesis is a prosthesis configured to output only mechanical force directly to tissue of a recipient.

45. The method of claim 17, wherein:
the captured vibrations are generated by a transducer of the prosthesis during said operation first travels through the middle ear of a recipient of the implanted prosthesis and then into the ear canal of the recipient to a device that captures the vibrations.

46. The method of claim 17, further comprising:
occluding an ear canal of the recipient of the implanted prosthesis, wherein
the action of capturing vibrations entails capturing the vibrations at a location in a space formed between a middle ear of the recipient and the location of occluding.

47. A method of evaluating an implanted prosthesis, comprising: operating the implanted prosthesis; capturing vibrations generated by a transducer of the prosthesis during said operation; comparing the captured vibration to a vibration model, wherein the vibrations travel from the transducer, through the recipient, to a vibration capture apparatus that captures the vibrations; and evaluating the performance of the implanted prosthesis based on the comparison; wherein: the prosthesis is a hearing prosthesis; the captured vibrations are captured sound; and the vibration model is a sound model; wherein: the action of operating the implanted prosthesis entails providing the implanted prosthesis with a stimulus signal that does not include an acoustic signal in the form of sound traveling through air to a microphone of the prosthesis.

48. The system of claim 35, wherein:
the vibration module is a model based on the ideal output from the hearing prosthesis for a given vibrating component stimulation.

* * * * *